US009024112B2

(12) United States Patent
Yoshikawa et al.

(10) Patent No.: US 9,024,112 B2
(45) Date of Patent: May 5, 2015

(54) METHOD FOR PROMOTION OF FLOWERING IN ROSACEAE FRUIT TREES USING APPLE LATENT SPHERICAL VIRUS VECTOR

(75) Inventors: Nobuyuki Yoshikawa, Iwate (JP); Noriko Yamagishi, Iwate (JP); Shintaro Sasaki, Iwate (JP); Sadao Komori, Iwate (JP); Masato Wada, Iwate (JP); Norimitsu Tanaka, Iwate (JP)

(73) Assignee: Incorporated National University Iwate University, Morioka-Shi, Iwate (JP)

( * ) Notice: Subject to any disclaimer, the term of this patent is extended or adjusted under 35 U.S.C. 154(b) by 63 days.

(21) Appl. No.: 13/201,286

(22) PCT Filed: Feb. 12, 2010

(86) PCT No.: PCT/JP2010/052098
§ 371 (c)(1),
(2), (4) Date: Oct. 28, 2011

(87) PCT Pub. No.: WO2010/093024
PCT Pub. Date: Aug. 19, 2010

(65) Prior Publication Data

US 2012/0090053 A1 Apr. 12, 2012

(30) Foreign Application Priority Data

Feb. 13, 2009 (JP) ................................ 2009-031642

(51) Int. Cl.
*C12N 15/82* (2006.01)
*A01H 5/00* (2006.01)
*A01H 3/00* (2006.01)

(52) U.S. Cl.
CPC ................ *C12N 15/827* (2013.01); *A01H 3/00* (2013.01); *C12N 15/8203* (2013.01)

(58) Field of Classification Search
None
See application file for complete search history.

(56) References Cited

FOREIGN PATENT DOCUMENTS

| | | | | |
|---|---|---|---|---|
| WO | 99/53070 | 10/1999 | | |
| WO | WO 9953070 A1 * | 10/1999 | ............. | C12N 15/29 |
| WO | 2006/033014 | 3/2006 | | |
| WO | WO 2006033014 A2 * | 3/2006 | ........... | C07K 14/415 |

OTHER PUBLICATIONS

Li et al, 2004, Arch Virol., 149:1541-1558.*
Kardailsky et al, 1999, Science, 286:1962-1965.*
Hanke et al, 2007, Genes, Genomes and Genomics, 1:1-20.*
Gal-On et al, 1995, J. of General Virology, 76:3223-3227.*
Wada et al, 2008, Plant Cell Physiol., 49:s125, Abstract 410(3aJ02).*
International Search Report issued Mar. 9, 2010 in International (PCT) Application No. PCT/JP2010/052098.
Kosuke Yamagata et al., "Shiroinunazuna FT Idenshi o Hatsugen suru Ringo Shokyukei Sensai Virus Kansen ni yoru Sushu Shokubutsu no Kaika Sokushin", Jpn. J. Phytophathol., 2006, vol. 72, No. 4, pp. 283 to 284 (Abstract 308).
Wada M et al., Analysis of flowering genes in apple., Plant Cell Physiol., 2008, vol. 49, suppl., p. s125 (Abstract 410 (3aJ02).
Noriko Yamagishi et al., "Particle Gun o Mochiita Ringo Shokyukei Senzai Virus Sesshuho no Kento", Jpn. J. Phytopathol., 2008, vol. 74, No. 1, p. 49 (Abstract (6)).
Kobayashi Y et al., *Arabidopsis thaliana* FT (Flowering Locus T) mRNA, complete cds., GenBank Accession AB027504, Feb. 13, 2004 [updated online], [retrieved from the Internet (retrieved on Feb. 25, 2010)] http://www.ncbi.nlm.nih.gov/sviewer/viewer.fcgi?4903011:OLD04:10265146.
Li C et al., Stable expression of foreign proteins in herbaceous and apple plants using Apple latent spherical virus RNA2 vectors., Arch. Virol., 2004, vol. 149, p. 1541-1558.

* cited by examiner

*Primary Examiner* — Ashwin Mehta
*Assistant Examiner* — Jason Deveau Rosen
(74) *Attorney, Agent, or Firm* — Wenderoth, Lind & Ponack, L.L.P.

(57) ABSTRACT

A novel means for accelerating the flowering time in Rosaceae fruit trees such as apples and pears is provided, by inoculating a viral RNA into a cotyledon of a Rosaceae fruit tree seedling immediately after rooting with a particle gun technique, wherein the viral RNA is concentrated from a proliferating host infected with a recombinant apple latent spherical virus (FT-ALSV) expressing an *Arabidopsis* FT gene.

1 Claim, 2 Drawing Sheets

*Fig.1*

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 1

ccgctcgaga tgtctataaa tataagaga                                        29


<210> SEQ ID NO 2
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 2

tcccccggga agtcttcttc ctccgcagc                                        29
```

METHOD FOR PROMOTION OF FLOWERING IN ROSACEAE FRUIT TREES USING APPLE LATENT SPHERICAL VIRUS VECTOR

This application is a U.S. national stage of International Application No. PCT/JP2010/052098, filed Feb. 12, 2010.

TECHNICAL FIELD

The present invention relates to a method for promotion of flowering in Rosaceae fruit trees through ALSV vector-mediated introduction of *Arabidopsis* FT gene.

BACKGROUND ART

Plants, as sessile organisms, require acquiring a variety of information from the surroundings for development and growth in an optimum environment. Particularly, formation of floral buds represents one of the development program processes that signify the dramatic transition from vegetative growth to reproductive growth at the shoot apical meristem. For successful propagation by means of sexual reproduction, the timing that determines this transition is particularly important. For example, flowering in apples occurs after a very long vegetative growth stage spanning 6 to 12 years from the germination of the seeds. While this is genetically determined and the specific mechanism remains elusive, the long flowering time poses a serious obstacle in, for example, the variety improvement of apple.

It has been elucidated that the timing that initiates the flower and bud formation is controlled by both internal factors such as nutritional conditions, circadian rhythm, and plant growth stage, and environmental external factors such as temperature and photoperiod (Non-Patent Document 1). In recent years, diligent researches using the long-day plant *Arabidopsis thaliana* (hereinafter, *Arabidopsis*) as a model plant have proposed that the flower and bud formation is determined by four pathways promoting flower and bud formation, specifically photoperiodic, vernalization, gibberellin (GA), and autonomous pathways (Non-Patent Documents 2 to 4). Because the signals in these pathways complement one another as need arises, losing one of the functions does not completely inhibit the flower and bud formation. The signals for flower and bud formation are integrated by FLOWERING LOCUS T (FT) gene and SUPPRESSOR OF OVEREXPRESSION OF CO1 (SOC1) gene, and promote expression of flower-initiating APETALA1 (AP1) gene and LEAFY (LFY) gene and flowering (Non-Patent Documents 5 to 7). FT gene, a pathway integrator gene, is more strongly expressed in the photoperiodic floral bud promoting pathway, and the transcription control of this gene represents the most important step in regulating flower and bud formation.

FT gene was identified in 1991 through the analysis of flower and bud formation delayed mutants (Non-Patent Document 8). It is known that day-length changes are sensed at the leaves through the interaction of circadian clock and photoreceptor. Expression of CONSTANS (CO) gene is induced in the sieve tissue of leaves (Non-Patent Documents 6 and 9). Expression of CO gene promotes FT gene expression (Non-Patent Documents 10 to 14). It has been elucidated that the FT gene expressed in leaves transfers to the shoot apical meristem in the form of FT protein (Non-Patent Document 15). It has been confirmed that the FD gene specifically expressed at the shoot apices encodes a bZIP transcription factor, and that FD protein is localized at the nucleus (Non-Patent Documents 16 and 17). The control target of FD protein is the AP1 gene which regulates the mitosis in floral buds, and the FT protein binds to the FD protein to promote the AP1 gene transcription activity and flower and bud formation (Non-Patent Documents 16 and 18).

It has also been elucidated that the *Arabidopsis* TERMINAL FLOWER 1 (TFL1) gene, highly homologous to FT gene, represses flower and bud formation, in contrast to FT gene (Non-Patent Documents 19 and 20). This is because TFL1 gene, highly homologous to FT gene, is antagonistic to FT gene, and binds to the FD protein to inhibit the AP1 gene transcription activity (Non-Patent Document 21). It has been demonstrated through creation of a transformant from a TFL1 gene-deactivated mutant that repressing the TFL1 gene expression promotes flower and bud formation (Non-Patent Document 22). In a recent report, a mutant produced by introducing an antisense strand of apple TFL1 (MdTFL1) gene has been shown to actually promote flower and bud formation in apple, presumably through silencing of TFL1 gene (Non-Patent Document 23). The regulation of the gene expression by RNA silencing is considered to provide an effective means for a genetic approach to explain the regulatory mechanism of flower and bud formation.

Apple latent spherical virus (ALSV) is a virus with a diameter of 25 nm, composed of a segmented, single-stranded RNA genome (RNA1 and RNA2), and three coat proteins (Vp25, Vp20, Vp24). Aside from apples, the virus is known to latently infect five species of *Solanaceae* plants [*Nicotiana tabacum* cv. Xanthi nc (hereinafter, *nicotiana*), *Nicotiana glutinosa* (hereinafter, glutinosa), *Nicotiana occidentalis* (hereinafter, occidentalis), *Nicotiana benthamiana*, Petunia], and *Arabidopsis* (Non-Patent Document 24). ALSV systemically infects the experimental plant *Chenopodium quinoa* (hereinafter, quinoa), and causes symptoms of vein clearing and chlorotic mottles (Non-Patent Documents 25 and 26), and symptoms of chlorotic mottles in soybeans in early stages of infection. There have been reports of infectious cDNA clones that include repeated protease cleavage sites between the ALSV-RNA2 product intercellular movement protein (MP) and Vp25, and in which a foreign gene transfer site is added (Non-Patent Documents 27 to 30). Expression of a foreign gene in infected plants using such clones is also reported (Patent Document 2, Non-Patent Documents 27, 31, and 32). ALSV has a highly advantageous characteristic as a virus vector, because the virus is capable of latent infection in nearly all hosts including apples. ALSV thus has great potential in many applications, including introduction and expression of various useful genes, post-genomic analyses using VIGS, and apple breeding using an original host.

[Patent Document 1] JP-A-2008-211993

[Patent Document 2] JP-A-2004-65009 (Expression of Foreign Gene in Apple)

[Non-Patent Document 1] Hastings M H, Follett B K. 2001. *Toward a molecular biological calendar?*, Journal of Biological Rhythms 16, 424-430.

[Non-Patent Document 2] Boss P K, Bastow R M, Mylne J S, Dean C. 2004. *Multiple pathways in the decision to flower: enabling, promoting, and resetting*. The Plant Cell 16, S18-S31.

[Non-Patent Document 3] Corbesier L, Coupland G. 2005. *Photoperiodic flowering of Arabidopsis: integrating genetic and physiological approaches to characterization of the floral stimulus*. Plant, Cell and Environment 28, 54-66.

[Non-Patent Document 4] Searle I, Coupland G. 2004. *Induction of flowering by seasonal changes in photoperiod*. The EMBO Journal 23, 1217-1222.

[Non-Patent Document 5] Moon J, Sus S S, Lee H, Choi K R, Hong C B, Peak N C, Kim S G, Lee I. 2003. *The SOC1 MADS-box gene integrates vernalization and gibberellin signals for flowering in Arabidopsis*. The Plant Journal 35, 613-623.

[Non-Patent Document 6] Pineiro M, Gomez-Mena C, Schaffer R, Martinez-Zapater J M, Coupland G. 2003. *EARLY BOLTING IN SHORT DAYS is related to chromatin remodelling factors and regulates flowering in Arabidopsis by repressing FT*. The Plant Cell 15, 1552-1562.

[Non-Patent Document 7] Takada S, Goto K. 2003. TERMINAL FLOWER2, an *Arabidopsis* homolog of HETEROCHROMATIN PROTEIN1, counteracts the activation of FLOWERING LOCUS T by CONSTANS in the vascular tissues of leaves to regulate flowering time. The Plant Cell 15, 2856-2865.

[Non-Patent Document 8] Koornneef M, Hanhart C J, van der Veen J H. 1991. *A genetic and physiological analysis of late flowering mutants in Arabidopsis thaliana*. Mol Gen Genet. 229, 57-66.

[Non-Patent Document 9] An H, Roussot C, Suarez-Lopez P, Corbesier L, Vincent C, Pineiro M, Hepworth S, Mouradov A, Justin S, Turnbull C, Coupland G. 2004. *CONSTANS acts in the phloem to regulate a systemic signal that induces photoperiodic flowering of Arabidopsis*. Development 131, 3615-3626.

[Non-Patent Document 10] Imaizumi T, Schultz T F, Harmon F G, Ho L A, Kay S A. 2005. *FKF1 F-box protein mediates cyclic degradation of a repressor of CONSTANS in Arabidopsis*. Science 309, 293-297.

[Non-Patent Document 11] Imaizumi T, Tran H G, Swartz T E, Briggs W R, Kay S A. 2003. *FKF1 is essential for photoperiodic-specific light signalling in Arabidopsis*. Nature 426, 302-306.

[Non-Patent Document 12] Suarez-Lopez P, Wheatley K, Robson F, Onouchi H, Valverde F, Coupland G. 2001. *CONSTANS mediates between the circadian clock and the control of flowering in Arabidopsis*. Nature 410, 1116-1120.

[Non-Patent Document 13] Valverde F, Mouradov A, Soppe W, Ravenscroft D, Samach A, Coupland G. 2004. *Photoreceptor regulation of CONSTANS protein in photoperiodic flowering*. Science 303, 1003-1006.

[Non-Patent Document 14] Yanovsky M J, Kay S A. 2002. *Molecular basis of seasonal time measurement in Arabidopsis*. Nature 419, 308-312.

[Non-Patent Document 15] Corbesier L, Vincent C, Jang S, Formara F, Fan Q, Searle I, Giakountis A, Farrona S, Gissot G, Turnbull C, Coupland G. 2007. *FT Protein Movement Contributes to Long-Distance Signaling in Floral Induction of Arabidopsis*. Science 316, 1030-1033.

[Non-Patent Document 16] Abe M, Kobayashi Y, Yamamoto S, Daimon Y, Yamaguchi A, Ikeda Y, Ichinoki H, Notaguchi M, Goto K, Araki T. 2005. *FD, a bZIP protein mediating signals from the floral pathway integrator FT at the shoot apex*. Science 309, 1052-1056.

[Non-Patent Document 17] Jakoby M, Weisshaar B, Droge-Laser W, Vicente-Carbajosa J, Tiedemann J, Kroj T, Parcy F. 2002. *bZIP transcription factors in Arabidopsis*. Trends in Plant Science 7, 106-111.

[Non-Patent Document 18] Wigge P A, Kim M C, Jaeger K E, Busch W, Schmid M, Lohmann J U, Weigel D. 2005. *Integration of spatial and temporal information during floral induction in Arabidopsis*. Science 309, 1056-1059.

[Non-Patent Document 19] Hanzawa Y, Money T, Bradley D. 2005. *A single amino acid converts a repressor to an activator of flowering*. Proc Natl Acad Sci USA 102, 7748-7753.

[Non-Patent Document 20] Kotoda N, Wada M. 2005. MdTFL1, a TFL1-like gene of apple, retards the transition from the vegetative to reproductive phase in transgenic *Arabidopsis*. Plant Science 168, 95-104.

[Non-Patent Document 21] Ahn J H, Miller D, Winter V J, Banfield M J, Lee J H, Yoo S Y, Henz S R, Brady R L, Weigel D. 2006. *A divergent external loop confers antagonistic activity on floral regulators FT and TFL1*. The EMBO Journal 25, 605-614

[Non-Patent Document 22] Shannon S, Meeks-Wagner D R. 1991. *A Mutation in the Arabidopsis TFL1 Gene Affects Inflorescence Meristem Development*. The Plant Cell 3, 877-892.

[Non-Patent Document 23] Kotoda N, Iwanami H, Takahashi S, Abe K. 2006. *Antisense expression of MdTFL1, a TFL1-like gene, reduces the juvenile phase in apple*. J Amer Soc Hort Sci 131, 74-81.

[Non-Patent Document 24] A. Igarashi. 2007. *Induction of RNA Silencing in Plant Endogenous Gene Using Apple Latent Spherical Virus Vector* (in Japanese), Graduate School of Agriculture, Iwate University, Master's Thesis.

[Non-Patent Document 25] T. Ito, H. Koganezawa, K. Yoshida. 1992. Back Transmission of Apple Russet Ring A Virus, an Isometric Virus Isolated from an Apple Tree with Fruit Russet Ring and Leaf Pucker Symptoms, to Apple Seedlings (in Japanese), Japanese Journal of Phytopathology 58, 617.

[Non-Patent Document 26] T. Ito. 1997. *The Etiology of Apple Russet Ring Disease* (in Japanese), Japanese Journal of Phytopathology 63, 487.

[Non-Patent Document 27] Li C, Sasaki N, Isogai M, Yoshikawa N. 2004. Stable expression of foreign proteins in herbaceous and apple plants using Apple latent spherical virus RNA2 vectors. Arch Virol 149, 1541-1558.

[Non-Patent Document 28] Li C, Yoshikawa N, Takahashi T, Ito T, Yoshida K, Koganezawa H. 2000. *Nucleotide sequence and genome organization of apple latent spherical virus: a new virus classed into the family Comoviridae*. Journal of General Virology 81, 541-547.

[Non-Patent Document 29] Li C. 1999. *Ringo kara bunrisareta shoukyukei wirusu no bunruigakuteki kenkyu* (in Japanese), Graduate School of Agriculture, Iwate University, Master's Thesis.

[Non-Patent Document 30] Li C. 2003. *Ringo shoukyukei senzai wirusu kouzou no genome to wirusu bekuta heno kathen ni kansuru kenkyu* (in Japanese), The United Graduate School of Agricultural Sciences, Iwate University, Doctoral Thesis.

[Non-Patent Document 31] N. Sasaki. 2003. *ALSV bekuta ni yoru koukinsei pepuchido no shokubutsutai deno hatsugen* (in Japanese), Faculty of Agriculture, Iwate University, Graduation Thesis.

[Non-Patent Document 32] N. Sasaki. 2005. *GFP de tagu shita ringo shoukyukei senzai wirusu no saiboukan oyobi choukyori ikou no kaiseki* (in Japanese), Graduate School of Agriculture, Department of Bioscience and Technology, Iwate University, Master's Thesis.

DISCLOSURE OF INVENTION

Problems to be Solved by the Invention

Rosaceae fruit trees such as apples and pears, the major fruits in Japan, typically take 6 to 12 years to flower after inoculation. This is one of the main reasons that makes the breeding (variety improvement) of apple and pear difficult.

The genetic mechanism involved in flower and bud formation in apple has recently been elucidated, and, as described above, there are reports that repressing the expression of the apple TFL1 gene that represses flower and bud formation promotes flower and bud formation in apple. In one report, a transgenic apple was created from the apple variety Ourin by introducing an antisense strand of TFL1 gene using a leaf disc method, and by culturing the tissue and regenerating the shoot. The shoot was then grafted to a dwarf stock, and grown in a greenhouse. The transgenic apple developed flowers in 8 to 25 months after being placed in the greenhouse, compared to about 6 years (69 months) for non-transgenic apples grown under the same conditions in a greenhouse (Non-Patent Document 23). However, as it currently stands, transformation of apple requires huge labor and a long time for tissue culturing and shoot regeneration. Further, transformation efficiency is low (0.15% for the apple described in Non-Patent Document 23), and transformation is limited to only certain apple varieties. Further, because the introduced gene in the transgenic apple is passed to the next generation, the current environment strictly regulating the use of transgenic plants does not allow the use of the next-generation individuals directly in breeding, even when a transgenic apple with accelerated flowering producing such individuals are obtained.

On the other hand, virus vector-mediated introduction of a foreign gene into a plant is easier and quicker than the transformation procedure, because it is established upon the infection and proliferation of the foreign gene-incorporated virus in plant. Effective virus vectors satisfy, for example, the requirement not to cause serious disease symptoms in the infected plant, and the requirement to stably proliferate in the infected plant. ALSV vector satisfies all of these requirements. Specifically, infection by ALSV vector is symptom free and does not cause disease in apple, and systemic infection is stably maintained. While techniques for introducing a foreign gene using ALSV vector is known (for example, Patent Document 2), a technique that promotes flowering in Rosaceae fruit trees using the ALSV vector technique is not available anywhere. Stable virus inoculation to fruits is generally difficult, and a method that can efficiently inoculate ALSV to apples and other Rosaceae fruit trees has not been established. This has become a big obstacle in using the ALSV vector-based foreign gene transfer technique in Rosaceae fruit trees. However, as noted above, ALSV vector has excellent characteristics as a virus vector for apples and other Rosaceae fruit trees. While ALSV undergoes seed transmission, the seed transmission frequency is low. This allows screening for virus-free individuals from the next generation of apples modified to show promoted flowering by the ALSV vector technique. Because the screened virus-free individuals are no different from the apples not having the gene introduced therein, these individuals can be directly used for breeding. Under these circumstances, establishment of a flowering promoting method for apples and other Rosaceae fruit trees using the ALSV vector technique is expected to provide a practical technique that has immediate use.

The present invention has been made under these circumstances, and an object of the invention is to provide a novel method for promoting flowering in apples and other Rosaceae fruit trees.

Means for Solving the Problems

In order to solve the foregoing problems, the present invention provides a method for promoting flowering of Rosaceae fruit trees, which comprises the step of inoculating a viral RNA into a cotyledon of a Rosaceae fruit tree seedling immediately after rooting with a particle gun technique, wherein the viral RNA is concentrated from a proliferating host infected with a recombinant apple latent spherical virus (FT-ALSV) expressing an *Arabidopsis* FT gene.

The invention also provides a virus-free individual or a seed thereof, which is screened from the next-generation individuals of the Rosaceae fruit tree of which flowering is promoted by the method.

Advantage of the Invention

With the present invention, the flowering of apples and pears, which typically takes 6 to 12 years, can be greatly shortened to 1.5 to 3 months. This enables efficient variety improvement in Rosaceae fruit trees, including apples and pears.

The virus-free individuals screened from the next-generation individuals of the Rosaceae fruit tree subjected to any of the foregoing methods and showing promoted flowering are no different from apple individuals not having the gene introduced therein. Thus, the screened individuals and seeds thereof can be directly used for breeding.

BRIEF DESCRIPTION OF DRAWINGS

FIG. 1 is a photographic image of apple seedlings with the flowers developed after about 1.5 months from FT-ALSV inoculation.

MODE FOR CARRYING OUT THE INVENTION

Figure 2:
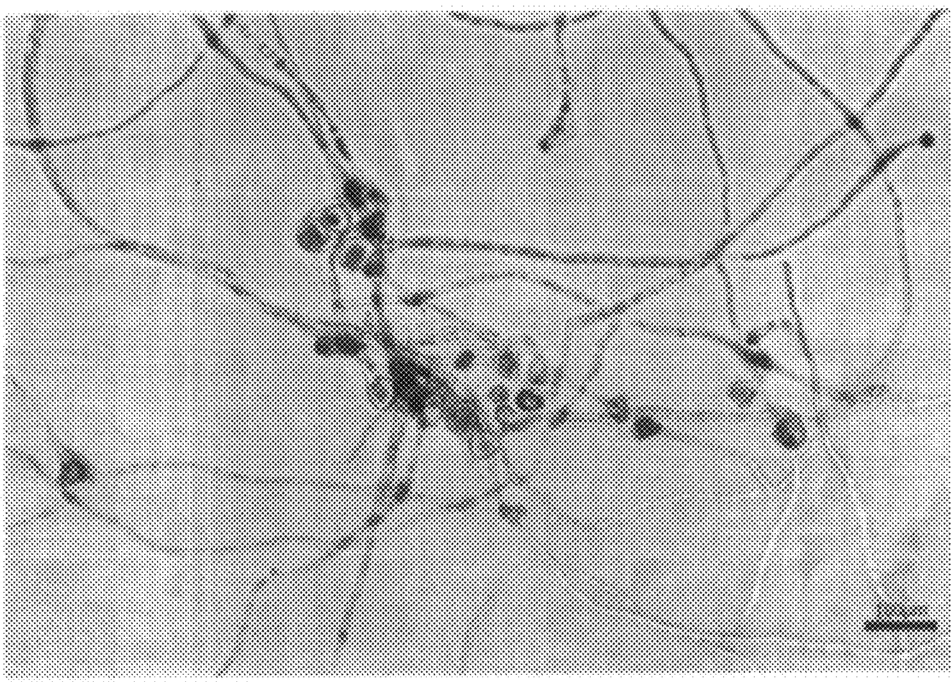
FIG. 2 represents germination of pollens collected from the flower of an FT-ALSV-infected apple individual; the pollen germination rate of this individual is about 80%.

As used herein, "Rosaceae fruit trees" refers to fruits belonging to the sub-family Maloideae of the family Rosaceae, including apples, pears, and loquats.

*Arabidopsis* FT gene can be obtained based on the known sequence information (GenBank/AB027504), using known methods such as RT-PCR that uses the total RNA of *Arabidopsis* as a template, and plaque hybridization using the *Arabidopsis* cDNA library. Specifically, *Arabidopsis* FT gene can easily be obtained according to the procedure described in Example below.

Basically, the FT gene-expressing recombinant ALSV vector (FT-ALSV) can be produced according to the method disclosed in Patent Document 2. Specifically, FT gene cDNA is inserted to the foreign gene transfer site of the ALSV RNA2 infectious cDNA clone pEALSR2L5R5 to construct pEALSR2L5R5FT. The construct is then inoculated into a proliferating host with the ALSV RNA1 infectious cDNA clone pEALSR1 to obtain the viral FT-ALSV.

The FT-ALSV is then concentrated from the FT-ALSV-infected quinoa leaves, and the extracted RNA from the concentrated sample is inoculated into the cotyledon of a Rosaceae fruit tree seedling using the particle gun technique. In this way, FT-ALSV-infected seedlings can be created at almost 100% efficiency, and the flowering of Rosaceae fruit trees such as apples can be greatly accelerated. In the present invention, the particle gun inoculation of FT-ALSV can be performed according to the following procedure.

Step (1): FT-ALSV is inoculated into a proliferating host (for example, quinoa).

Step (2): FT-ALSV is extracted from the infected leaves of the proliferating host, and concentrated by treatment such as centrifugation.

Step (3): RNA is isolated from the concentrated FT-ALSV.

Step (4): The RNA is inoculated into the cotyledon of a Rosaceae fruit tree seedling immediately after rooting, using the particle gun technique.

This procedure is described in detail in Example below, and can be performed in the manner described therein. One of the characteristics of this method is that the RNA isolated from the FT-ALSV in step (3) is used for inoculation, and that the RNA is inoculated into the cotyledon of a Rosaceae fruit tree seedling in step (4).

The cotyledon of a Rosaceae fruit tree seedling immediately after rooting used in step (4) is prepared as follows. First, the seed coat of the seed of the seedling immediately after rooting following dormancy is removed with a surgical knife to expose the cotyledon. The cotyledon is then inoculated with an RNA-applied microcarrier using a particle gun. The inoculation of FT-ALSV by this procedure infects Rosaceae fruit tree seedlings at 100% efficiency.

The seed inoculated with RNA is left unattended for 2 to 3 days under shaded, maintained humidity conditions. After being gradually adjusted to ambient air, the seed is transplanted to a culture soil, and grown at an ordinary growth temperature (about 25° C.).

In the case of the apple described in Example below, about 40% of the individuals in the Rosaceae fruit trees grown in this manner flowered in 1.5 to 3 months.

The present invention is described below in more detail based on Example. It should be noted, however, that the present invention is in no way limited by the following examples.

EXAMPLE 1

1. Materials and Methods (1) Construction of FT-ALSV Infectious cDNA Clone

The 525-bp FT protein-expressing region (Base Number: 70 to 594) of *Arabidopsis* FT gene (864 bp, accession number: AB027504) was amplified as follows. For the DNA amplification, a plasmid (pBSAtFT-19) having incorporated the sequence (Base Number: 29 to 709) of FT mRNA at the XbaI/SacI sites of pBlue script II SK (+) was used as a template, and 10 μM FT-Xho (+) [5'-CCGCTCGAGATGTCTATAAATATAAGAGA-3'] (SEQ ID NO: 1), and 10 μM FT-Sma (−) [5'-TCCCCCGGGAAGTCTTCTTCCTCCGCAGC-3'] (SEQ ID NO: 2) were used as the plus-strand primer and the minus-strand primer, respectively. A mixture containing 1 μl of a template DNA solution (10 ng/μl), the plus-strand and minus-strand primers (2 μl each), 1.6 μl of a 2.5 mM dNTP mixture (TaKaRa), 2 μl of 10× Ex Taq Buffer (TaKaRa), 11.2 μl of sterile water, and 0.2 μl of TaKaRa Ex Taq was prepared. The mixture was then treated at 94° C. for 5 min using GeneAmp PCR System 2400 (Perkin Elmer), followed by 35 cycles of reaction [94° C., 30 sec→55° C., 30 sec→72° C., 60 sec]. PCR was finished after treatment at 72° C. for 7 min, and finally at 4° C. for 5 min. One microliter of a loading buffer [0.25% bromophenol blue, 1 mM EDTA (pH 8.0), 40% sucrose] was then added to 1 μl of the PCR product, and the mixture was electrophoresed by being applied to the wells of a 1% agarose gel prepared with 0.15 g of Agarose S (Nippon Gene), 15 ml of TAE [40 mM Tris, 20 mM acetic acid, 1 mM EDTA (pH 8.0)], and 0.6 μl of ethidium bromide. The result confirmed that the amplified DNA was of the size expected from the FT gene.

The amplified FT gene was cut with XhoI and SmaI, as follows. First, a mixture containing a 10 μl solution of the PCR-amplified FT gene, 10 μl of 10×K Buffer (TaKaRa), 78 μl of sterile water, and 2 μl of XhoI (TaKaRa) was prepared, and left unattended at 37° C. for 2 hours. Then, 100 μl of sterile water, 100 μl of TE [10 mM Tris-HCl (pH 8.0), 1 mM EDTA (pH 8.0)] saturated phenol, and 100 μl of chloroform were successively added to the reaction liquid. The mixture was stirred for 30 seconds using a vortex mixer, and centrifuged at 14,000 rpm for 5 min (4° C.). After adding an equal amount of chloroform to 200 μl of the supernatant, the mixture was stirred for 30 seconds using a vortex mixer, and centrifuged at 14,000 rpm for 5 min (4° C.). Two hundred microliters of the supernatant was transferred to a separate 1.5 ml-volume tube. After adding 20 μl of 3 M sodium acetate (pH 5.2) and 600 μl of 99% ethanol, the supernatant was sufficiently stirred, and left unattended at −80° C. for 30 min. One milliliter of 70% ethanol was added to the precipitate obtained after centrifugation at 14,000 rpm for 10 min (4° C.), and the mixture was centrifuged at 14,000 rpm for 5 min (4° C.). The supernatant was discarded, and the precipitate was dried under reduced pressure, and suspended in 50 μl of sterile water. The solution was then mixed with 10 μl of 10×T Buffer (TaKaRa), 10 μl of 0.1% BSA (TaKaRa), 28 μl of sterile water, and 2 μl of SmaI (TaKaRa), and the mixture was left unattended at 25° C. for 2 hours. After restriction enzyme treatment, 100 μl of sterile water, 100 μl of TE saturated phenol, and 100 μl of chloroform were added to the reaction liquid. The mixture was stirred for 30 seconds using a vortex mixer, and centrifuged at 14,000 rpm for 5 min (4° C.). After adding an equal amount of chloroform to 200 μl of the supernatant, the mixture was stirred for 30 seconds using a vortex mixer, and centrifuged at 14,000 rpm for 5 min (4° C.). After the centrifugation, 20 μl of 3 M sodium acetate (pH 5.2) and 600 μl of 99% ethanol were added to 200 μl of the supernatant. The mixture was sufficiently stirred, and left unattended at −80° C. for 30 min. One milliliter of 70% ethanol was then added to the precipitate obtained after centrifugation at 14,000 rpm for 10 min (4° C.), and the mixture was centrifuged at 14,000 rpm for 5 min (4° C.). After discarding the supernatant, the precipitate was dried under reduced pressure, and suspended in 20 μl of sterile water. The XhoI and SmaI enzyme treatment was also performed in the same manner for 10 μl of the infectious cDNA done pEALSR2L5R5 (100 ng/μl) having incorporated a foreign gene transfer site in ALSV-RNA2.

The FT gene and pEALSR2L5R5 after the restriction enzyme treatment were collected using a QIA quick Gel Extraction Kit (QIAGEN). After adding 2 μl of 10× loading buffer to 18 μl of an FT gene solution, the mixture was applied to the wells of a 1% agarose gel for electrophoresis. The target DNA fragment was then cut out from the agarose gel using a surgical knife, and placed in a 1.5 ml-volume tube to weigh the gel. A buffer QG with three times the volume of the gel was added to the 1.5 ml-volume tube, and heated to 50° C. to completely dissolve the gel. The solution was yellow in color. The gel was then mixed with an equal amount of isopropanol, and the gel solution was placed in a column set on a 2 ml-volume tube, and centrifuged at 10,000 rpm for 1 min (room temperature). The solution fell down into the 2 ml-volume tube was discarded, and 750 μl of buffer PE was added to the column for washing. After centrifugation at 10,000 rpm for 1 min (room temperature), the solution fell down into the 2 ml-volume tube was discarded again. After being centrifuged at 10,000 rpm for 1 min (room temperature), the column was set on a new 1.5 ml-volume tube, and 30 μl of buffer EB [10 mM Tris-HCl (pH 8.5)] was added to the center of the column for DNA elution. The mixture was left unattended for 1 min, and centrifuged at 13,000 rpm for 1 min (room temperature).

After the gel collection, the FT gene was used as insert DNA for ligation with the plasmid vector pEALSR2L5R5. A mixture containing 4 μl of insert DNA solution and 1 μl of plasmid vector solution was prepared, and left unattended at 16° C. for 2 hours after adding 5 μl of solution I of TaKaRa DNA Ligation Kit Ver. 2.1. The mixture was used as a ligation solution after adding 1.1 μl of solution III.

Transformation was performed using the heat shock method. Competent cells (100 μl) preserved at −80° C. were slowly thawed in ice, slowly mixed with 5 μl of the ligation solution over the course of 5 seconds, and left unattended in ice for 30 min. The cell solution was then heated at 42° C. for 45 seconds using a water bath, and cooled in ice for 2 min. Then, 900 μl of pre-heated SOC [2% tryptone, 0.5% yeast extract, 0.058% NaCl, 0.019% KCl, 10 mM $MgCl_2$, 10 mM $MgSO_4$, 20 mM glucose] was added in a clean bench. After placing a lid and wrapping a parafilm, the cell culture was shaken at 37° C. for 1 hour using a shaking incubator. Then, 200 μl of the culture was dropped onto an LMA plate [1% tryptone, 0.5% yeast extract, 0.058% NaCl, 10 mM $MgSO_1$, 1.5% agar, 40 mg/ml ampicillin], applied over a medium surface using a spreader, and dried for 10 min with the petri dish uncovered. The remaining culture (800 μl) was centrifuged at 14,000 rpm for 30 seconds, and the remaining 200 μl after discarding the supernatant (600 μl) was used to suspend the precipitate. Then, as above, 100 μl of the solution was dropped onto an LMA plate, applied over a medium surface with a spreader, and dried for 10 min with the lid removed. After the medium was dried, each plate was placed in an incubator, and cultured at 37° C. for 12 to 16 hours.

Sixteen test tubes containing 2 ml of LB culture [1% tryptone, 0.5% yeast extract, 1% NaCl] used for the small-scale culturing of the transformed colonies were prepared. After autoclaving, 40 µl of 1:10 dilution of ampicillin [25 mg/ml] was added to each test tube. The colonies were scraped with the tip of a sterilized toothpick, and contacted with an LMA plate to inoculate a part of *Escherichia coli* and create a master plate. The toothpick was left in the test tube containing LB culture. The master plate was numbered according to each colony, statically cultured overnight at 37° C., and preserved at 4° C. after being sealed with a vinyl tape. The test tubes with LB culture were also given the same numbers corresponding to the master plates. After being tilted and shake-cultured overnight at 37° C., the total amount in each of the sixteen test tubes was transferred to a corresponding 1.5 ml-volume tube numbered accordingly, and centrifuged at 14,000 rpm for 1 min (room temperature). The procedure below was performed for each of the sixteen 1.5 ml-volume tubes. The supernatant was removed with an aspirator, and 350 µl of STET [0.1 M NaCl, 10 mM Tris-HCl (pH 8.0), 1 mM EDTA (pH 8.0), 5% Triton X-100] was added and mixed to suspend the precipitate. The suspension was stirred for 3 seconds after adding 25 µl of a lysozyme solution prepared as a 10 mg/ml solution in 10 mM Tris-HCl (pH 8.0), and cooled in ice for 5 min after being boiled for 40 seconds. The suspension was then centrifuged at 14,000 rpm for 10 min (room temperature), and the precipitate was removed using a sterilized toothpick. The remaining supernatant was stirred after adding 40 µl of 3 M sodium acetate (pH 5.2) and 420 µl of isopropanol, and left unattended at room temperature for 5 min. The mixture was centrifuged at 14,000 rpm for 5 min (4° C.), and the supernatant was carefully removed. After adding 500 µl of 70% ethanol to the precipitate, the mixture was centrifuged at 14,000 rpm for 5 min (4° C.) to remove the supernatant, and the precipitate was dried under reduced pressure. Then, 50 µl of TE adjusted to make RNase 20 µg/ml was added to suspend the precipitate, and the suspension was used as a plasmid solution after being left unattended at 37° C. for 30 min.

Introduction of the FT gene into the plasmid obtained by small-scale culturing was confirmed by restriction enzyme treatment. First, 2 µl of the plasmid solution, 1 µl of 10×K Buffer (TaKaRa), 6.8 µl of sterile water, and 0.2 µl of XhoI (TaKaRa) were transferred to a new 1.5 ml-volume tube, mixed, and left unattended at 37° C. for 2 hours. Thereafter, 90 µl of sterile water, 50 µl of TE saturated phenol, and 50 µl of chloroform were added in order, stirred for 30 seconds with a vortex mixer, and centrifuged at 14,000 rpm for 5 min (4° C.). After adding an equal amount of chloroform to 100 µl of the supernatant, the mixture was stirred for 30 seconds with a vortex mixer, and centrifuged at 14,000 rpm for 5 min (4° C.). The supernatant (100 µl) was then transferred to a separate 1.5 ml-volume tube. Thereafter, 10 µl of 3 M sodium acetate (pH 5.2) and 300 µl of 99% ethanol were added to the supernatant, sufficiently stirred, and left unattended at −80° C. for 30 min. The mixture was then centrifuged at 14,000 rpm for 10 min (4° C.), and 500 µl of 70% ethanol was added to the resulting precipitate before further centrifugation at 14,000 rpm for 5 min (4° C.). After discarding the supernatant, the precipitate was dried under reduced pressure, and suspended in 10 µl of sterile water. The solution was mixed with 2 µl of 10×T Buffer (TaKaRa), 2 µl of 0.1% BSA (TaKaRa), 5.6 µl of sterile water, and 0.4 µl of SmaI (TaKaRa), and the mixture was left unattended at 25° C. for 2 hours. Thereafter, 1 µl of 10× loading buffer was added to 9 µl of the plasmid solution treated with XhoI and SmaI, and the mixture was applied to the wells of a 1% agarose gel for electrophoresis. The electrophoresis looked for a sample with a fragment that had the same size as that of the PCR-amplified FT gene and was cut out from the plasmid. The number for this sample was recorded, and the colony corresponding to this number was used for the next large-scale culturing.

For large-scale culturing, a 100-ml LB culture supplemented with ampicillin (200 µl), and QIAGEN Plasmid Midi Kit (100; QIAGEN) were used. Single colonies were collected from the master plate using a toothpick, and placed in the LB culture contained in a Sakaguchi flask. After being shake-cultured at 37° C. for 12 to 16 hours, the culture (50 ml) was transferred to a Falcon tube, and centrifuged at 7,500 rpm for 15 min (4° C.). The supernatant was discarded, and the remaining 50 ml was centrifuged in the same manner. Then, the pellet was suspended in RNase-containing buffer P1 (4 ml). After adding buffer P2 (4 ml), the suspension was sufficiently mixed by being inverted 4 to 6 times, and was left unattended for 5 min at room temperature. After adding cooled buffer P3 (4 ml), the suspension was mixed by being inverted 4 to 6 times, and incubated on ice for 15 min. The solution was then transferred to a 50 ml-volume centrifuge tube, and centrifuged at 13,000 rpm (Hitachi RPR16 rotor) for 30 min (4° C.) to collect the supernatant that contained plasmid DNA. The supernatant was further centrifuged at 13,000 rpm for 15 min (4° C.). Thereafter, buffer QBT (4 ml) was added to the column, and the column was equilibrated with the buffer allowed to free fall to empty the column. The supernatant obtained after centrifugation was then added to the column to impregnate a resin. The column was then washed twice with buffer QC (10 ml), and the DNA was eluted to a new Falcon tube with buffer QF (5 ml). Then, 3.5 ml of isopropanol was added and mixed with the eluted DNA solution, and the mixture was centrifuged at 11,000 rpm for 30 min (4° C.) immediately after being placed in a COREX tube (Hitachi RPR16 rotor). The supernatant was quickly removed by decantation. The precipitated DNA was washed with 70% ethanol (2 ml), and centrifuged at 11,000 rpm for 10 min (4° C.). The precipitated DNA after the removal of the supernatant was then dried under reduced pressure, and dissolved in 100 µl of TE. The DNA concentration was adjusted to 1 µg/µl using a spectrophotometer (ND-1000 v3.1.2), and an infectious cDNA clone pEALSR2L5R5FT was obtained that included the FT gene introduced to pEALSR2L5R5.

(2) Creation of Viral Infectious cDNA Clone

The ALSV RNA1 infectious cDNA clone pEALSR1 (1 µg/µl) purified from the large-scale culture was prepared according to the method of (1). Carborundum was sprinkled over the leaves of the proliferating host *Chenopodium quinoa* (hereinafter, quinoa), and each leaf was inoculated with 8 µl of a DNA solution as a mixture of equal parts of pEALSR1 (1 µg/µl) and pEALSR2L5R5FT (1 µg/µl) to obtain a viral, FT gene-expressing ALSV vector (FT-ALSV). Quinoa leaves that showed the chlorotic symptom after the FT-ALSV infection were sampled, and used for the subsequent procedure.

(3) Concentrating Virus

The FT gene-ligated ALSV (FT-ALSV) was concentrated according to the following procedure. After the inoculation of *Chenopodium quinoa* (hereinafter, quinoa) with FT-ALSV, sampling was made from the leaves 7 to 10 days post inoculation and from the upper leaves that showed disease symptoms. Then, 300 ml of extraction buffer [0.1 M Tris-HCl (pH 7.8), 0.1 M NaCl, 5 mM $MgCl_2$] and 3 ml of mercaptoethanol were added to 100 g of the infected leaves, and the leaves were milled with a Waring blender. The milled solution was filtered through a double gauze, and centrifuged at 9,000 rpm for 10 min (4° C.) (Hitachi RPR12-2 rotor). A bentonite solution (40 mg/ml) was then gently added to the resulting solution while being stirred, and the mixture was centrifuged at 9,000 rpm for 10 min (4° C.). This procedure was repeated for clarification until the supernatant turned transparent yellow. Thereafter, polyethylene glycol was added to the supernatant at a concentration of 8%, and the mixture was stirred in ice for 1 hour. After centrifugation at 9,000 rpm for 10 min (4° C.), the precipitate was dissolved in a 20-ml extraction buffer. The mixture was then stirred for 15 min (4° C.) after adding 10 ml of chloroform, and centrifuged at 9,000 rpm for 10 min (4° C.) (Hitachi RPR16 rotor). The supernatant was then centrifuged at 45,000 rpm for 1.5 hours (4° C.) (Hitachi RP65 rotor). Thereafter, 1 ml of extraction buffer was added to the precipitate to sufficiently suspend the precipitate. The suspension was centrifuged at 9,000 rpm for 10 min (4° C.), and the supernatant was used as concentrated FT-ALSV.

(4) RNA Extraction

RNA was extracted from the concentrated FT-ALSV, and used for the preparation of a microcarrier. The extraction of RNA from the concentrated FT-ALSV was performed according to the following procedure. First, 150 μl of sterile water was added to 50 μl of the concentrated FT-ALSV, and stirred therein. Then, the mixture was sufficiently stirred with a vortex mixer after adding water-saturated phenol and chloroform (100 μl each). After being centrifuged at 14,000 rpm for 5 min (4° C.), the supernatant (200 μl) was transferred to a new 1.5 ml-volume tube, and sufficiently stirred after adding 20 μl of 3 M sodium acetate (pH 5.2) and 500 μl of 99% ethanol. The mixture was then left unattended at −80° C. for 15 min. Thereafter, 1 ml of 70% ethanol was added to the precipitate obtained after centrifugation at 14,000 rpm for 15 min (4° C.), and the mixture was centrifuged at 14,000 rpm for 5 min (4° C.). The supernatant was discarded to make a suspension in 15-μl sterile water. The resulting solution was adjusted to 1 μg/μl using a spectrophotometer (ND-1000 v3.1.2), and used as an RNA solution.

(5) Particle Gun Inoculation (Biolistic PDS-1000/He Particle Delivery System (Bio-Rad))

A microcarrier (RNA; 3 μg/gold particle; 0.4 mg/shot) was prepared according to the following procedure. First, 2.4 mg of gold particles (0.6 μm) were weighed into a 1.5 ml-volume tube, and sufficiently stirred with a vortex mixer after adding 100 μl of sterile water. The tube was placed in an ultrasonic bath and sonicated for 5 min. With the tube set on a vortex mixer, 18 μl of the RNA solution (1 μg/μl) was gently added to the tube while being stirred. This was followed by addition of 5 M ammonium acetate (11.8 μl) and then isopropanol (259.6 μl), added gently in the same manner. The mixture was stirred for a while, and left unattended at −20° C. for at least 1 hour. After removing the supernatant, the gold particle precipitate was stirred momentarily with a vortex mixer. Then, 1 ml of 100% ethanol was added to the gold particle precipitate, and the mixture was gently shaken without disrupting the precipitate, before removing the supernatant. This procedure was repeated four times, and the gold particles were suspended in 60 μl of 100% ethanol. The suspension (10 μl) was applied and spread over about 1 cm at the center of the microcarrier, and, after being sufficiently dried, introduced into a plant using a particle gun. For the inoculation test using a particle gun, 4 to 6 apple seeds immediately after rooting were used as a test group. The seed coat was removed with a surgical knife, and concentrically placed on a petri dish. A total of 4 shots were made to the cotyledon in each test group at a helium pressure of 1,100 psi, using Biolistic PDS-1000/He Particle Delivery System (Bio-Rad).

(6) Particle Gun Inoculation (Helios Gene Gun System (Bio-Rad))

A microcarrier (RNA; 3 μg/gold particle; 0.4 mg/shot) was prepared according to the following procedure. First, 7.2 mg of gold particles (1.0 μm) were weighed into a 1.5 ml-volume tube, and sufficiently stirred with a vortex mixer after adding 100 μl of sterile water. The tube was placed in an ultrasonic bath and sonicated for 5 min. With the tube set on a vortex mixer, 54 μl of the RNA solution (1 μg/μl) was gently added to the tube while being stirred. This was followed by addition of 5 M ammonium acetate (15.4 μl) and then isopropanol (338.8 μl), added gently in the same manner. The mixture was stirred for a while, and left unattended at −20° C. for at least 1 hour. After removing the supernatant, the gold particle precipitate was stirred momentarily with a vortex mixer. Then, 1 ml of 100% ethanol was added to the gold particle precipitate, and the mixture was gently shaken without disrupting the precipitate, before removing the supernatant. This procedure was repeated four times, and the gold particles were suspended in 1,080 μl of 100% ethanol, and used for the preparation of a gold-coated tube. With a gold-coated tube (BIO-RAD) set on a tubing prep-station (BIO-RAD), inside of the gold-coated tube was completely dried by flowing pure nitrogen gas for 20 min. Then, the gold particle suspension was uniformly charged into the gold-coated tube, and left unattended for 5 min to deposit the gold particles on the gold-coated tube. The supernatant 99.5% ethanol was then removed from the gold-coated tube. Thereafter, while uniformly scattering the gold particles inside the gold-coated tube by the rotation of the tubing prep-station, pure nitrogen gas was flown through the gold-coated tube to completely dry the gold particles. The gold-coated tube was then cut into 18 pieces with a tube cutter (BIO-RAD) for introduction into a plant using a particle gun. The seed coat of apple seeds immediately after rooting was removed with a surgical knife to inoculate the cotyledon. A total of 4 shots were made for each individual at a helium pressure of 220 psi, using Helios Gene Gun System (Bio-Rad).

(7) Growth of Inoculated Individuals

The inoculated individuals were left unattended for 2 to 3 days under shaded, maintained humid conditions. After being gradually adjusted to ambient air, the plants were transplanted to a culture soil, and grown in an incubator (25° C.; light period, 16 hours; dark period, 8 hours).

(8) Pollen Germination Test

The pollen germination rate was determined from the proportion of the pollens that showed pollen tube elongation in at least 120 pollens observed for each flower under a light microscope after the pollens were sprayed onto a 1% agar medium supplemented with 17% sucrose and left unattended for at least 12 hours in an incubator.

2. Results

Figure 1:
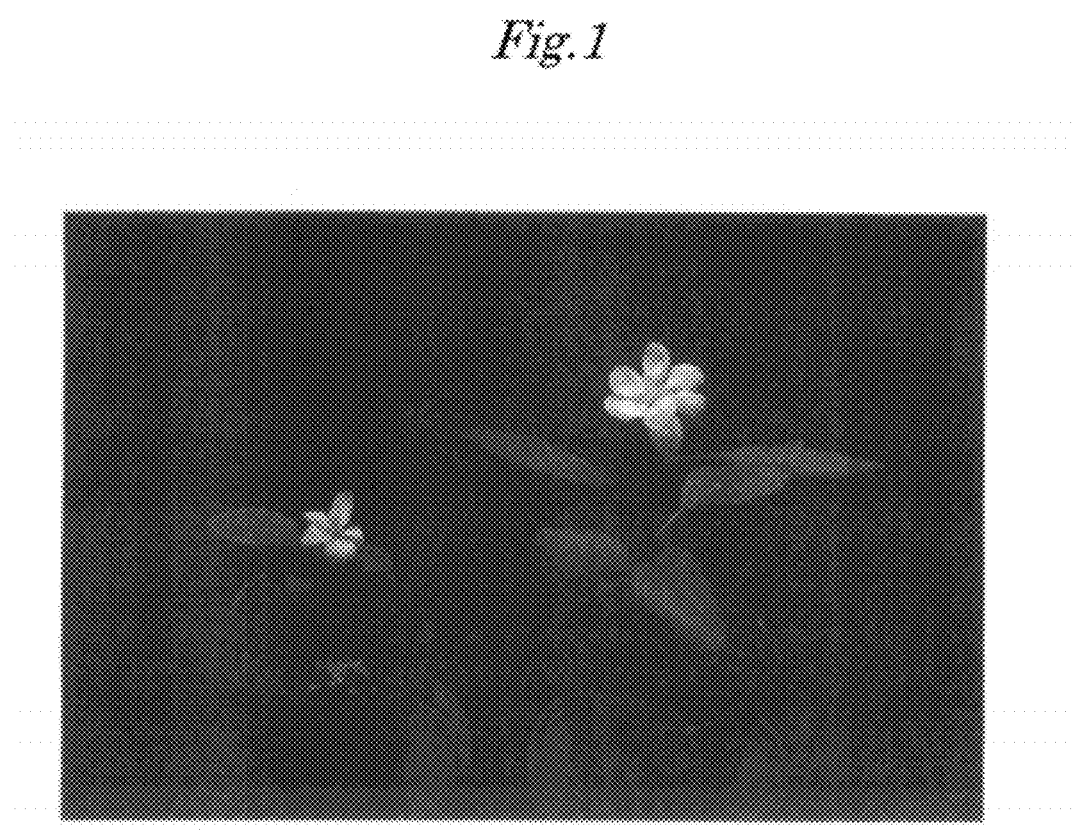

The inoculation of the RNA extracted from concentrated FT-ALSV to the cotyledon of apple seedlings immediately after rooting using the particle gun technique confirmed the systemic FT-ALSV infection in 20 out of the all 20 individuals inoculated. The result thus revealed that the technique can be used for the infection of apple with the ALSV vector at very high efficiency. Eight out of the twenty individuals confirmed infected with FT-ALSV had flowers in a 1.5- to 3-months time after the inoculation, as shown in FIG. 1. The results of the germination test conducted with the pollens collected from each flowering individual revealed that the pollens of all individuals had germination capability, with the highest germination rate as high as close to 80%, as shown in FIG. 2. Specifically, the use of FT-ALSV is considered to greatly reduce the flowering time in apples, which typically requires 6 to 12 years to flower. It is also considered possible that the apple with the FT-ALSV-induced accelerated flowering time can be used as a pollen parent.

INDUSTRIAL APPLICABILITY

As described in detail above, the present invention can greatly reduce the flowering time of Rosaceae fruit trees, including apples and pears. The invention thus greatly contributes to the variety improvement of Rosaceae fruit trees such as apples and pears.

The invention claimed is:

1. A method for promotion of flowering 1.5 to 3 months after seeding of a Rosaceae fruit tree, which comprises exposing a cotyledon of a Rosaceae fruit seed immediately after rooting by removing the seed coat; and inoculating a viral RNA into the cotyledon with a particle gun technique, wherein the viral RNA is concentrated from a proliferating host infected with a recombinant apple latent spherical virus (FT-ALSV) expressing an *Arabidopsis* FT gene.

* * * * *